United States Patent
Akins et al.

(10) Patent No.: US 12,017,012 B2
(45) Date of Patent: Jun. 25, 2024

(54) APPARATUS AND METHODS TO MODULATE STYLET STIFFNESS PROFILE

(71) Applicant: Bard Access Systems, Inc., Salt Lake City, UT (US)

(72) Inventors: Samuel Akins, Draper, UT (US); Teresa Tam Ta, Murray, UT (US); Gidon Ofek, Millcreek, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 282 days.

(21) Appl. No.: 16/781,326

(22) Filed: Feb. 4, 2020

(65) Prior Publication Data

US 2020/0246588 A1    Aug. 6, 2020

Related U.S. Application Data

(60) Provisional application No. 62/801,585, filed on Feb. 5, 2019.

(51) Int. Cl.
*A61M 25/01* (2006.01)
*A61B 5/0538* (2021.01)
*A61M 25/00* (2006.01)

(52) U.S. Cl.
CPC .... *A61M 25/0102* (2013.01); *A61M 25/0053* (2013.01); *A61M 25/0158* (2013.01);
(Continued)

(58) Field of Classification Search
CPC .. A61M 2025/0166; A61M 2025/0063; A61M 25/0102; A61M 25/0053;
(Continued)

(56) References Cited

U.S. PATENT DOCUMENTS

| | | | | |
|---|---|---|---|---|
| 4,967,753 A | * | 11/1990 | Haase | A61B 8/12 600/463 |
| 5,144,959 A | * | 9/1992 | Gambale | A61M 25/09 604/170.01 |

(Continued)

FOREIGN PATENT DOCUMENTS

| | | |
|---|---|---|
| EP | 2085108 A2 | 8/2009 |
| WO | 2002043798 A1 | 6/2002 |

(Continued)

OTHER PUBLICATIONS

PCT/US20/16540 filed Feb. 4, 2020 International Search Report and Written Opinion dated Apr. 28, 2020.
(Continued)

*Primary Examiner* — Jason E Flick
*Assistant Examiner* — Adam J. Cermak
(74) *Attorney, Agent, or Firm* — Rutan & Tucker LLP

(57) ABSTRACT

A stylet for use in guiding a catheter to a predetermined location within the body of a patient includes a continuous core member for transmitting an electrical signal from a distal section of the stylet to a proximal end. The stylet includes a differing stiffness profile along its length. The differing stiffness characteristics are achieved by varying the number of strands of a wire, the diameter of each individual strand, twisting or braiding the strands, or varying the number of turns per unit length of the twisted strands. The stiffness of the stylet may decrease intermittently or continuously from the proximal end to the distal section. By using multiple strands bundled together, the beneficial conductive and, optionally, magnetic properties can be maximized while at the same time the stiffness characteristics can be modified.

13 Claims, 7 Drawing Sheets

US 12,017,012 B2

Page 2

(52) U.S. Cl.
CPC .... *A61B 5/0538* (2013.01); *A61M 2025/0063* (2013.01); *A61M 2025/0166* (2013.01)

(58) Field of Classification Search
CPC .......... A61M 25/0158; A61M 25/0127; A61M 2025/09191; A61B 5/0538; A61B 5/283
See application file for complete search history.

(56) References Cited

U.S. PATENT DOCUMENTS

| | | | |
|---|---|---|---|
| 5,833,631 A * | 11/1998 | Nguyen | A61M 25/09 600/585 |
| 6,142,958 A | 11/2000 | Hammarstrom et al. | |
| 6,165,140 A | 12/2000 | Ferrera | |
| 6,183,420 B1 | 2/2001 | Douk et al. | |
| 6,432,066 B1 | 8/2002 | Ferrera | |
| 6,440,088 B1 * | 8/2002 | Jacobsen | A61M 25/09 600/585 |
| 6,464,650 B2 | 10/2002 | Jafari et al. | |
| 6,491,648 B1 | 12/2002 | Cornish et al. | |
| 6,562,021 B1 | 5/2003 | Derbin et al. | |
| 6,572,538 B2 | 6/2003 | Takase | |
| 6,579,246 B2 | 6/2003 | Jacobsen et al. | |
| 6,595,932 B2 | 7/2003 | Ferrera | |
| 6,602,207 B1 | 8/2003 | Mam et al. | |
| 6,616,996 B1 | 9/2003 | Keith et al. | |
| 6,652,472 B2 | 11/2003 | Jafari et al. | |
| 6,726,700 B1 | 4/2004 | Levine | |
| 6,805,676 B2 | 10/2004 | Klint | |
| 6,841,214 B1 | 1/2005 | Keith et al. | |
| 6,918,882 B2 | 7/2005 | Skujins et al. | |
| 6,936,065 B2 | 8/2005 | Khan et al. | |
| 7,014,616 B2 | 3/2006 | Ferrera | |
| 7,074,197 B2 | 7/2006 | Reynolds et al. | |
| 7,097,624 B2 | 8/2006 | Campion et al. | |
| 7,309,318 B2 * | 12/2007 | Cassell | A61M 25/09 600/585 |
| 7,322,944 B2 | 1/2008 | Osawa et al. | |
| 7,618,379 B2 * | 11/2009 | Reynolds | A61L 31/022 604/524 |
| 7,713,215 B2 * | 5/2010 | Shriver | A61M 25/09 600/585 |
| 7,715,903 B2 | 5/2010 | Hartley et al. | |
| 7,783,333 B2 | 8/2010 | Brister et al. | |
| 7,828,832 B2 | 11/2010 | Belluche et al. | |
| 7,881,769 B2 | 2/2011 | Sobe | |
| 7,883,474 B1 * | 2/2011 | Mirigian | A61M 25/09 600/585 |
| 7,969,142 B2 * | 6/2011 | Krueger | G01D 5/208 324/207.16 |
| 8,043,232 B2 | 10/2011 | Osborne | |
| 8,043,312 B2 | 10/2011 | Noriega et al. | |
| 8,267,872 B2 * | 9/2012 | Ressemann | A61M 25/09025 600/585 |
| 8,308,658 B2 | 11/2012 | Albers et al. | |
| 8,353,850 B2 * | 1/2013 | Ressemann | A61M 25/09025 600/585 |
| 8,414,506 B2 | 4/2013 | Reynolds et al. | |
| 8,721,588 B2 | 5/2014 | Echarri et al. | |
| 8,812,072 B2 | 8/2014 | Brister et al. | |
| 8,888,773 B2 | 11/2014 | Chang et al. | |
| 8,936,558 B2 | 1/2015 | Jacobsen et al. | |
| 8,956,310 B2 | 2/2015 | Miyata et al. | |
| 8,996,095 B2 | 3/2015 | Anderson et al. | |
| 9,017,268 B2 | 4/2015 | Miyata et al. | |
| 9,636,031 B2 * | 5/2017 | Cox | A61M 25/0108 |
| 9,669,188 B2 | 6/2017 | Echarri et al. | |
| 9,750,532 B2 | 9/2017 | Toomey et al. | |
| 9,901,714 B2 * | 2/2018 | Lemon | A61M 25/0102 |
| 9,968,761 B2 | 5/2018 | Brecker | |
| 10,039,903 B2 * | 8/2018 | Kay | A61M 25/09 |
| 10,071,229 B2 | 9/2018 | Simpson et al. | |
| 2002/0177870 A1 | 11/2002 | Sepetka et al. | |
| 2003/0069521 A1 * | 4/2003 | Reynolds | A61M 25/09 600/585 |
| 2004/0054301 A1 * | 3/2004 | Cassell | A61M 25/09 600/585 |
| 2004/0111044 A1 * | 6/2004 | Davis | A61M 25/09016 600/585 |
| 2005/0027212 A1 * | 2/2005 | Segner | A61M 25/09 600/585 |
| 2006/0064036 A1 * | 3/2006 | Osborne | A61M 25/09 600/585 |
| 2006/0106445 A1 | 5/2006 | Woollett | |
| 2007/0049846 A1 * | 3/2007 | Bown | A61M 25/0102 600/585 |
| 2007/0185415 A1 * | 8/2007 | Ressemann | A61M 25/09025 600/585 |
| 2008/0183186 A1 | 7/2008 | Bly et al. | |
| 2008/0255446 A1 * | 10/2008 | Akins | A61M 25/01 600/585 |
| 2008/0312597 A1 * | 12/2008 | Uihlein | A61M 25/09 604/164.13 |
| 2009/0112128 A1 * | 4/2009 | Schiff | A61B 5/14539 600/585 |
| 2009/0192412 A1 * | 7/2009 | Sela | A61B 5/065 600/585 |
| 2009/0192413 A1 * | 7/2009 | Sela | A61M 25/09 600/585 |
| 2010/0145147 A1 * | 6/2010 | Pinsky | A61M 25/0127 600/114 |
| 2010/0318000 A1 | 12/2010 | Von Malmborg et al. | |
| 2011/0144625 A1 | 6/2011 | Mirigian et al. | |
| 2012/0035539 A1 * | 2/2012 | Tegg | A61M 25/0158 606/41 |
| 2013/0296691 A1 * | 11/2013 | Ashe | A61B 5/6848 600/424 |
| 2014/0187917 A1 * | 7/2014 | Clark | A61B 5/062 600/424 |
| 2014/0235982 A1 | 8/2014 | Brister et al. | |
| 2014/0276117 A1 | 9/2014 | Burkett | |
| 2015/0182168 A1 * | 7/2015 | Draper | A61L 29/06 600/381 |
| 2015/0320975 A1 | 11/2015 | Simpson et al. | |
| 2015/0352326 A1 * | 12/2015 | Tegg | A61M 25/0012 604/95.04 |
| 2016/0001038 A1 * | 1/2016 | Romo | A61M 25/0012 604/526 |
| 2016/0228180 A1 * | 8/2016 | Sliwa | A61B 18/1206 |
| 2016/0331942 A1 | 11/2016 | Minar et al. | |
| 2018/0071496 A1 * | 3/2018 | Snyder | A61M 25/09 |
| 2018/0085162 A1 | 3/2018 | Chang et al. | |
| 2018/0145443 A1 | 5/2018 | Andreason et al. | |
| 2018/0161546 A1 | 6/2018 | Aslam et al. | |
| 2018/0169389 A1 | 6/2018 | Lemon et al. | |
| 2018/0256860 A1 * | 9/2018 | Minar | A61M 25/09 |
| 2018/0296144 A1 | 10/2018 | Brister et al. | |
| 2018/0296799 A1 | 10/2018 | Horst et al. | |
| 2019/0025040 A1 * | 1/2019 | Andreason | A61B 5/062 |
| 2019/0054277 A1 * | 2/2019 | LaBelle | A61M 25/09033 |
| 2020/0163298 A1 | 5/2020 | Campau et al. | |

FOREIGN PATENT DOCUMENTS

| | | | | |
|---|---|---|---|---|
| WO | 2004009170 A1 | 1/2004 | | |
| WO | 2006034008 A2 | 3/2006 | | |
| WO | WO-2006034008 A2 * | 3/2006 | ............ | A61B 17/24 |
| WO | WO-2015116687 A1 * | 8/2015 | ......... | A61B 18/1492 |
| WO | 2017127722 A1 | 7/2017 | | |
| WO | 2017147041 A1 | 8/2017 | | |
| WO | WO-2017147041 A1 * | 8/2017 | ............ | A61M 25/09 |

OTHER PUBLICATIONS

EP 207524232.2 filed Aug. 26, 2021 Extended European Search Report dated Oct. 7, 2022.

* cited by examiner

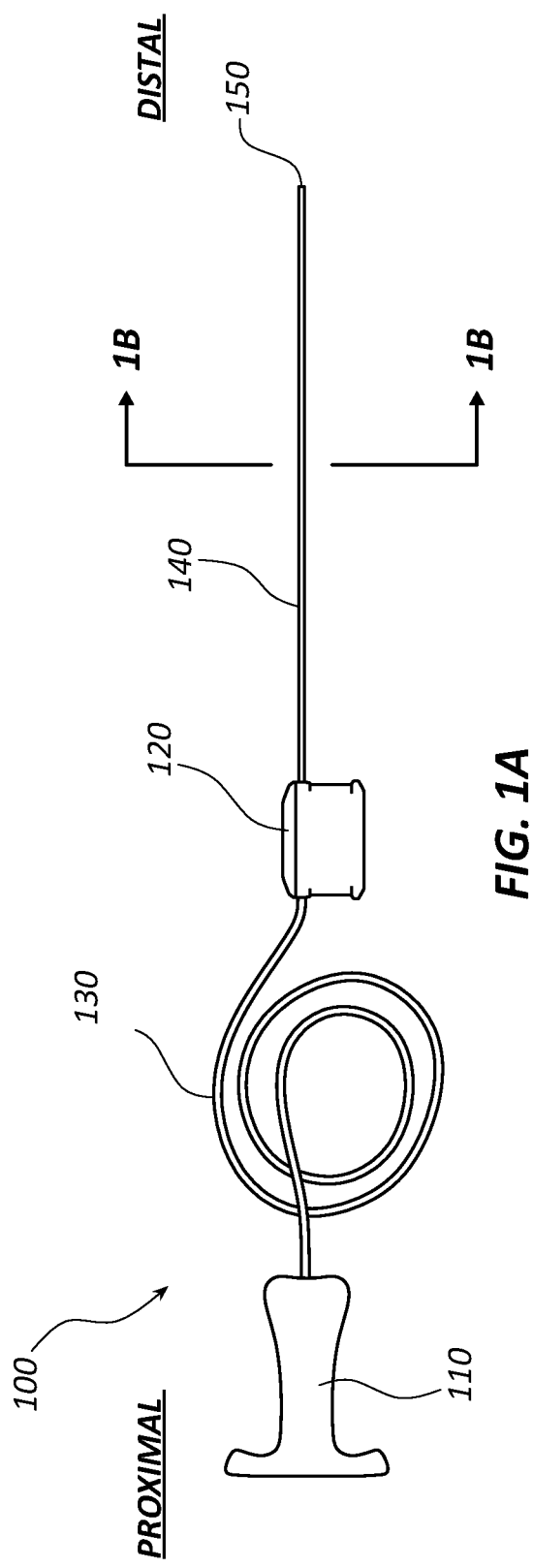
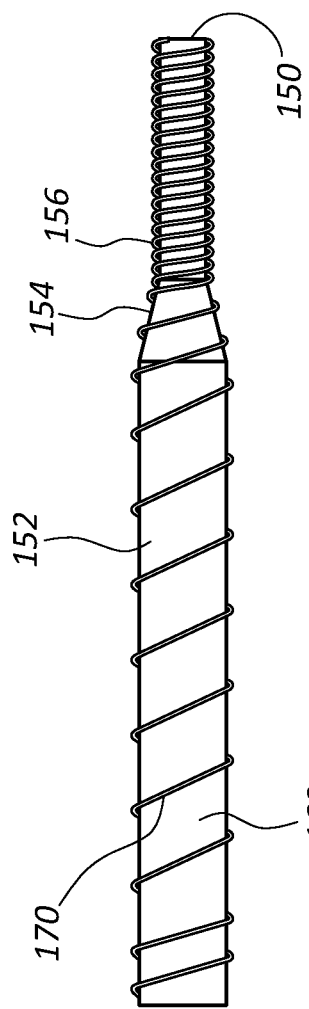
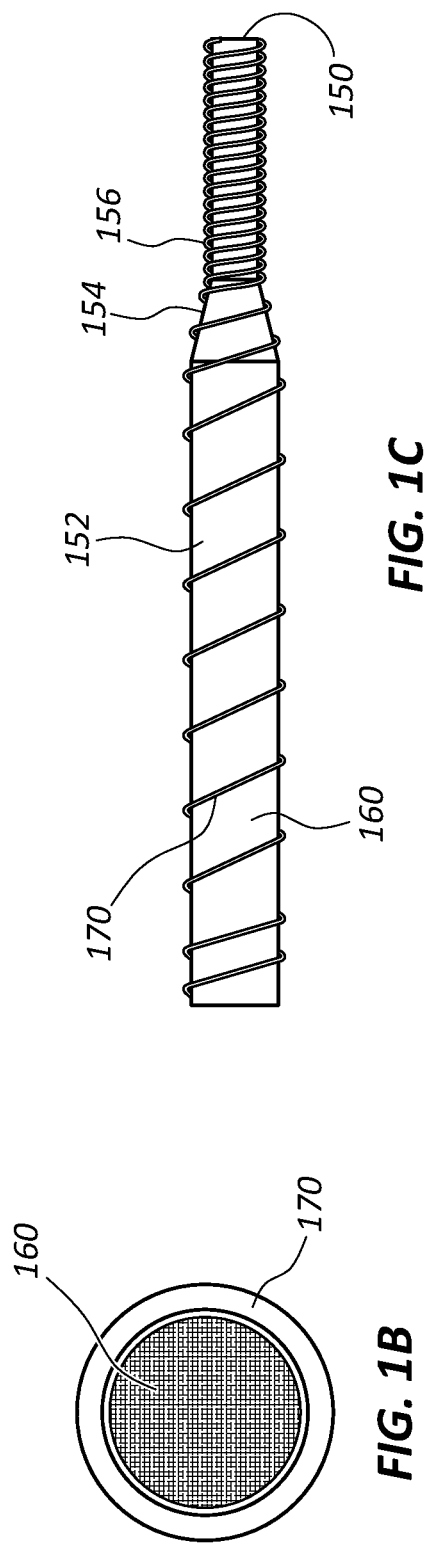
FIG. 1A
FIG. 1B
FIG. 1C

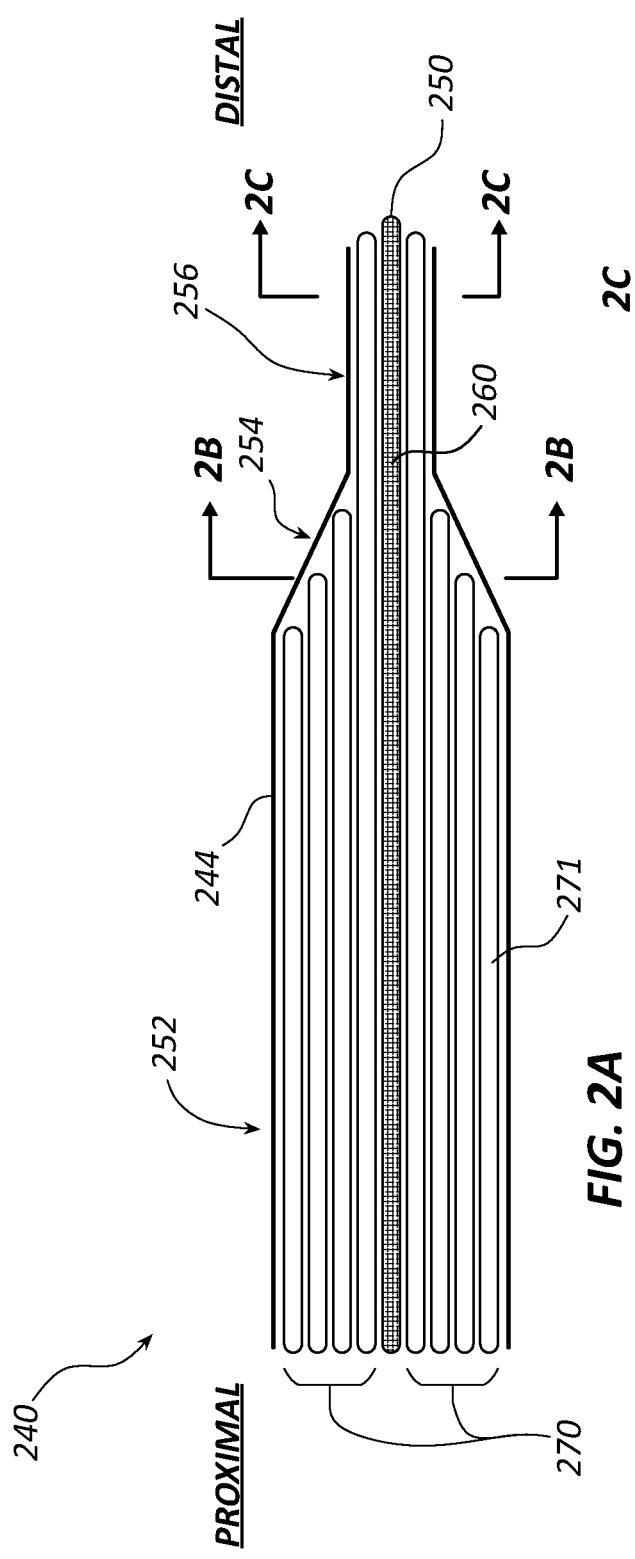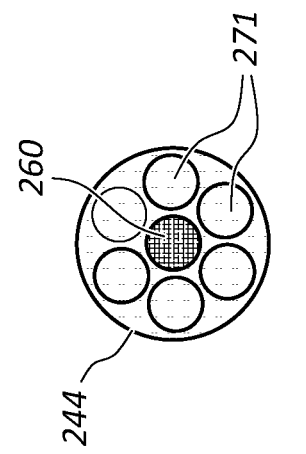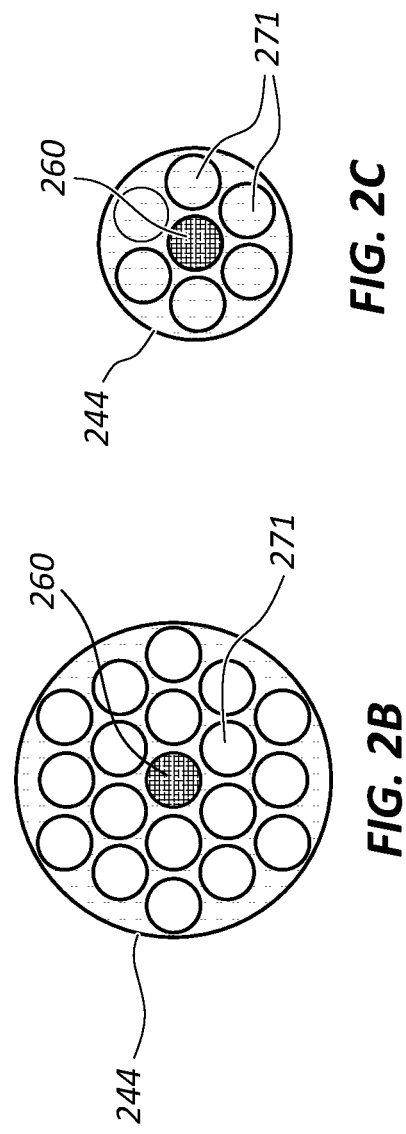
FIG. 2A
FIG. 2B
FIG. 2C

APPARATUS AND METHODS TO MODULATE STYLET STIFFNESS PROFILE

PRIORITY

This application claims the benefit of priority to U.S. Provisional Application No. 62/801,585 filed Feb. 5, 2019, which is incorporated by reference in its entirety into this application.

BACKGROUND

Stylets and similar medical devices are used in guiding a distal tip of a catheter to a predetermined location. Optionally, such medical devices are also being designed to provide tip tracking and confirmation functionality for catheter placement, "tracking stylets." Stylets require contrasting mechanical properties of both rigidity and flexibility, in order to be both manipulated by a clinician and to negotiate tortuous vascular pathways.

Stylet assemblies generally include a connector, a handle, a tether wire, a stylet wire, and a conductive tip. Where the stylet includes a tracking functionality, the tracking stylet wire includes a core wire and a magnetic element, e.g. a magnet wire. The core wire and conductive tip serves as a conductive path for the ECG signal from the patient's heart and is transmitted through the connector to an external tracking system. The magnet wire can be coiled around the core wire and transmits alternating current pulses, which generates a magnetic field for the system to track.

BRIEF SUMMARY

Briefly summarized, embodiments of the present invention are directed to a stylet for use in guiding a distal tip of a catheter to a predetermined location within the body of a patient. As used herein the term "stylet" is considered to encompass both tracking and non-tracking stylets, as well as variations thereof. In an aspect of the invention, stylets include novel materials that would otherwise be excluded due to their mechanical properties.

Disclosed herein is a stylet, including a core member extending from a proximal portion to a distal portion of the stylet, the core member configured to transmit an electrical signal from the distal portion to the proximal portion, and a magnetic element disposed about a portion of the core member, wherein a stiffness characteristic of the stylet differs along a longitudinal axis of the stylet.

In some embodiments, a material of the core member includes A228 carbon steel and a material of the magnetic element includes copper. In some embodiments, the stylet further includes a proximal portion defining a first stiffness characteristic, a distal portion defining a second stiffness characteristic, and a transition portion disposed therebetween. The proximal portion defines a first diameter, the distal portion defines a second diameter, less than the first diameter, and the transition portion includes a tapered outer surface extending from the first diameter to the second diameter. The magnetic element includes one or more wires coiled or braided around the core member. One of a wire diameter, a coil pitch, or the number of turns of the magnetic element differs along the longitudinal axis of the stylet.

In some embodiments, the magnetic element includes a plurality of wires extending parallel to the longitudinal axis of the stylet, the magnetic element defining one or more layers of the plurality of wires disposed about the core member, and including a sleeve disposed on an outer surface of the stylet. An outer layer of the magnetic element terminates proximally of an inner layer of the magnetic element to define a tapered outer profile. The plurality of wires of the magnetic element define a uniform longitudinal length.

In some embodiments, the magnetic element includes a plurality of wires, a first portion of the plurality of wires extend parallel to the longitudinal axis of the stylet, and a second portion of the plurality of wires include a coiled or braided portion, the first portion and the second portion define a uniform outer diameter. The first portion defines a first stiffness characteristic, and the second portion defines a second stiffness characteristic different from the first stiffness characteristic. In some embodiments, the magnetic element includes a first plurality of wires, extending parallel to the longitudinal axis and defining a first stiffness characteristic, each wire of the first plurality of wires defining a first diameter, and a second plurality of wires, extending parallel to the longitudinal axis and defining a second stiffness characteristic, each wire of the second plurality of wires defining a second diameter, less than the first diameter. The second plurality of wires includes a greater number of wires than the first plurality of wires such that an outer profile of the stylet defines a consistent outer diameter.

Also disclosed is an elongate medical device configured to be inserted into a vasculature of a patient, the medical device including, a core member having a proximal portion extending parallel to a longitudinal axis of the stylet and defining a first stiffness characteristic, and a distal portion including a plurality of wires, defining a second stiffness characteristic, and a magnetic element disposed on an outer surface of the core member.

In some embodiments, the proximal portion terminates in a tapered end and is coupled to the distal portion using one of a conductive adhesive, a non-conductive adhesive, a thermoplastic, an epoxy, a room-temperature-vulcanizing (RTV) silicone, soldering, welding, bonding, crimping, or press-fitting. In some embodiments, the elongate medical device further includes a sleeve disposed on an outer surface of the core member between the core member and the magnetic element, the magnetic element coiled or braided about the core member. The sleeve includes one of a polyimide jacket, or a heat shrink tube. The proximal portion is a single wire and the plurality of wires of the proximal portion is one of coiled, braided, or twisted about each other. In some embodiments, the elongate medical device further includes a sleeve disposed on an outer surface of the magnetic element and including a conductive tip disposed at a distal end of the distal portion. In some embodiments, the elongate medical device further includes a spring disposed on an outer surface of the core member, between the core member and the magnetic element, and extending from the proximal portion to the conductive tip.

Also disclosed is a method of making a stylet, including providing a core member extending from a proximal portion to a distal portion of the stylet, the core member configured to transmit an electrical signal from the distal portion to the proximal portion, disposing a magnetic element disposed about a portion of the core member, and modifying a stiffness characteristic of the stylet by modifying a stiffness characteristic of one of the magnetic element or the core member.

In some embodiments, the magnetic element includes a plurality of wires and modifying a stiffness characteristic of the stylet includes modifying one of a number, pitch of coil, number of turns, orientation relative to a longitudinal axis of the stylet, longitudinal length, or wire diameter. In some embodiments, the core element includes a one or more wire strands and modifying a stiffness characteristic of the stylet includes modifying one of a number, pitch of coil, number of turns, orientation relative to a longitudinal axis of the stylet, longitudinal length, or wire diameter of the one or more wire strands of the core member.

These and other features of embodiments of the present invention will become more fully apparent from the following description and appended claims, or may be learned by the practice of embodiments of the invention as set forth hereinafter.

BRIEF DESCRIPTION OF THE DRAWINGS

To further clarify embodiments of the disclosure, a more particular description will be rendered by reference to specific embodiments thereof that are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIGS. 1A-C are various views of a stylet according to one embodiment;

FIGS. 2A-C are various views of a stylet according to one embodiment;

Figure 3:
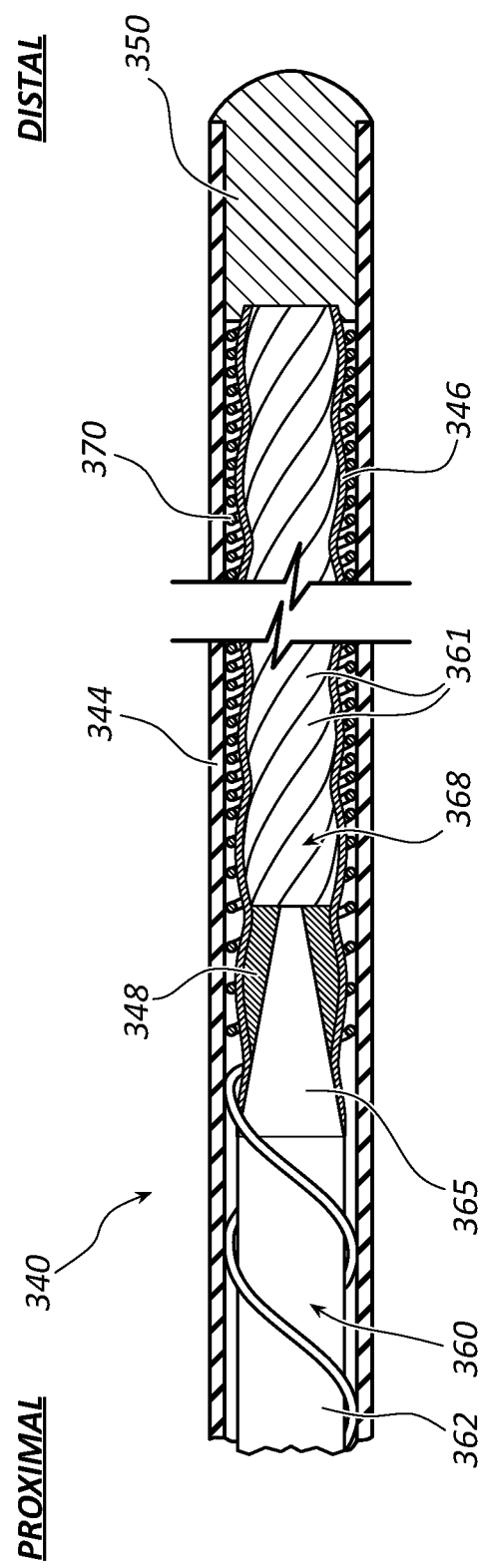
FIG. 3 is a side view of a stylet according to one embodiment.

While the present disclosure is subject to various modifications and alternative forms, specific embodiments thereof have been shown by way of example in the drawings and will herein be described in detail. The invention should be understood to not be limited to the particular forms disclosed, but on the contrary, the intention is to cover all modifications, equivalents, and alternatives falling within the spirit and scope of the present disclosure.

DETAILED DESCRIPTION

Reference will now be made to figures wherein like structures will be provided with like reference designations. It is understood that the drawings are diagrammatic and schematic representations of exemplary embodiments of the present invention, and are neither limiting nor necessarily drawn to scale.

Regarding terminology used herein, it should also be understood the terminology is for the purpose of describing some particular embodiments, and the terminology does not limit the scope of the concepts provided herein. Unless indicated otherwise, ordinal numbers (e.g., first, second, third, etc.) are used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. It should also be understood that, unless indicated otherwise, any labels such as "left," "right," "front," "back," "top," "bottom," "forward," "reverse," "clockwise," "counter clockwise," "up," "down," or other similar terms such as "upper," "lower," "aft," "fore," "vertical," "horizontal," "proximal," "distal," and the like are used for convenience and are not intended to imply, for example, any particular fixed location, orientation, or direction. Instead, such labels are used to reflect, for example, relative location, orientation, or directions. It should also be understood that the singular forms of "a," "an," and "the" include plural references unless the context clearly dictates otherwise.

For clarity it is to be understood that the word "proximal" refers to a direction relatively closer to a clinician using the device to be described herein, while the word "distal" refers to a direction relatively further from the clinician. For example, the end of a stylet placed within the body of a patient is considered a distal end of the stylet, while the stylet end remaining outside the body is a proximal end of the stylet. Further, the words "including," "has," and "having," as used herein, including the claims, shall have the same meaning as the word "comprising."

As used herein a "stiffness characteristic" can include various mechanical properties that describe the elasticity, malleability, durometer, rigidity, sheer strength, super-elasticity, shape memory, or any feature that describes an ability of a material to deform, either permanently or temporarily, without rupturing. Further, a "first" stiffness characteristic and a "second" stiffness characteristic can be different values of the same mechanical property, or stiffness characteristic, or can be different mechanical properties, or stiffness characteristics.

Unless defined otherwise, all technical and scientific terms used herein have the same meaning as commonly understood by those of ordinary skill in the art. In addition, it is noted that features of the stylets described herein are not exclusive to the described embodiment, i.e., a particular feature of one described embodiment could be incorporated into another described embodiment.

Stylets and similar medical devices are used in guiding a distal tip of a catheter to a predetermined location. Optionally, such medical devices are also being designed to provide tip tracking and confirmation functionality for catheter placement, "tracking stylets." As shown in FIG. 1, a stylet assembly 100 typically includes four major components: a connector 110, a handle 120, a tether wire 130, a stylet wire 140, and a conductive tip 150. Where the stylet includes a tracking functionality, the tracking stylet wire 140 includes a core wire 160 and a magnetic element, e.g., a magnet wire 170. The core wire 160 and conductive tip 150 serves as a conductive path for the ECG signal from the patient's heart and is transmitted through the connector to an external tracking system. The magnet wire 170 can be coiled around the core wire 160 and transmits alternating current pulses, which generates a magnetic field for the system to track. Systems and methods related to medical device tracking in a patient can be found, for example, in U.S. Pat. No. 9,636,031, filed Sep. 29, 2010, US 2018/0145443, filed Nov. 21, 2017, and US 2019/0025040, filed Jan. 20, 2017, each of which is incorporated by reference in its entirety into this application.

FIG. 1C shows detail of the stylet wire 140. The stylet wire 140 includes a proximal portion 152, a transition portion 154 and a distal portion 156. The proximal, transition, and distal portions 152, 154, 156 can display differing stiffness characteristics. Advantageously, the proximal portion 152 of the stylet 140 can have an increased stiffness profile to allow clinicians to easily handle and maneuver the stylet during catheter placement. Comparatively, the distal portion can have a more flexible stiffness profile to allow the stylet to navigate tortuous vascular pathways. For example, with regards stylet 140 a proximal portion 152 includes a core wire 160 that defines a first cross-sectional area, and a distal portion 156 that defines a second cross-sectional area. The first cross-sectional area being larger than the second cross-sectional area. A transition portion 154 of the core wire 160 defines a tapering cross-sectional area from the first cross-sectional area to a second cross-sectional area. In an embodiment, the core wire 160 is formed of a single material, accordingly the difference in cross-sectional areas defines differing stiffness profiles. A magnet wire 170 can then be coiled around the core wire 160. It will be appreciated that the pitch of the coils, or number of turns, of the magnet wire 170 can vary long the length of the stylet 140. For example, a proximal portion 152 can include a shallower pitch, or fewer turns, compared with the transition portion 154, or the distal portion 156. Optionally, the pitch of the coils can vary within a proximal, transition, or distal portions 152, 154, 156. The difference in pitch, or number of turns can affect the strength of the magnetic field, the stiffness characteristics of the stylet 140, or combinations thereof.

Embodiments of stylets are also disclosed that have a modulated stiffness profile along a length of the stylet. The stylet can incorporate materials, for example A228 carbon steel "music" wire, which have applications as either a stylet, or an electromagnetic tracking stylet, but would otherwise be rendered unsuitable for typical stylets due to the mechanical properties of such materials. As used herein, a stylet wire or core wire can be formed of stainless steel, carbon steel (e.g. ASTM A228 carbon music wire), or the like, or combinations thereof. As used herein, a magnet wire can be formed of copper, or similarly suitable conductive material.

The overall conductive resistance of a core wire or the magnetic strength of a magnet wire is dependent on the overall material mass of the wire used, with thicker wires displaying less conductive resistance or greater electromagnetic strength. However, thicker wires also display greater stiffness characteristics, which can be detrimental when negotiating tortuous vascular pathways. By using multiple strands of wires bundled together, the beneficial conductive and magnetic properties can be maximized while at the same time the stiffness characteristics can be minimized. Varying the number of wires, diameter of each individual wire strand, twisting or braiding the wires, varying the number of turns per unit length of the twisted wire, can all affect the stiffness characteristics of the wire bundle, while maintaining the beneficial conductive and magnetic properties.

FIGS. 2A-C illustrate one embodiment of a stylet 240. The stylet 240 includes a core wire 260 surrounded by one or more strands 271 of wires 270. It will be appreciated where stylet 240 includes electromagnetic tracking capabilities, one or more strands 271 of wires 270 can be a magnet wire. The total number of wires included in the stylet 240 can vary between 2 and 50, although it will be appreciated that greater numbers of wires can be included without deviating from the scope of the present invention. The diameter of the core wire 260 and each individual strand 271, can have an outer diameter of between 0.001 in. (0.0254 mm) and 0.100 in. (2.54 mm), with a preferred embodiment having an outer diameter of substantially 0.010 in. (0.254 mm). In an embodiment the core wire 260 and strands 271 can have the same diameter. In an embodiment the core wire 260 and strands 271 can have different diameters.

Each of the core wire 260 and the wires 270 extend between a proximal end and a distal end, along a longitudinal axis. As shown in FIGS. 2B-C, the wires 270 can be "bundled" around the core wire 260 in a hexagonal circle packing formation, although other configurations of circle packing are considered to fall within the scope of the present invention. As shown in FIG. 2A, the wires 270 can be arranged about the core 260 wire in layers. For example, FIG. 2B shows a two layer formation and FIG. 2C shows a single layer formation.

Each layer can extend from a proximal end of the stylet 240 to different distal points along the length of core wire 260. Inner layers of wire 270 can terminate distally of adjacent outer layers. A proximal portion 252 of the stylet 240 can include the most layers of wires 270 to define a first cross-sectional area. A distal portion 256 can include the fewest number of layers of wires 270 to define a second cross-sectional area. In an embodiment, a distal portion 256 can include only the core wire 260. Intermediate layers of wires 270 can terminate at different distal points to define a tapering profile of the stylet 240, e.g. transition section 254, from the first cross-sectional area to the second cross-sectional area. The different number of layers of wires 270 can provide different stiffness characteristics along the length of the stylet 240, while the core wire 260, being continuous along the entire length of stylet, provides a direct conductive pathway from a conductive tip 250 at the distal end to a connector 110 at a proximal end. In an embodiment, the intermediate layers of wires 270 can terminate at substantially the same distal position to define a stepped profile between the proximal portion 252 and the distal portion 256. Although only a single core wire 260 is shown, it will be appreciated that two or more strands of core wires can be included and fall within the scope of the present invention. The stylet 240 can further include a sleeve 244 disposed on an outer surface thereof, for example, a heat shrink sleeve or polyimide sleeve, or the like. The sleeve can maintain the core wire 260 and wires 270 in the "bundled" formation.

FIG. 3 illustrates one embodiment of a stylet 340. The stylet 340 includes a core wire 360 and a magnet wire 370. The core wire 360 includes a straight portion 362, extending longitudinally and formed of a single monolithic wire, the straight portion terminating in a tapered end 365. The tapered end 365 can be coupled with a twisted portion 368 of core wire 360. The twisted portion 368 can include two or more strands 361 of core wire twisted or braided about each other. The twisted portion 368 can be coupled 348 with the tapered end 365 using, for example, adhesives, such as conductive or non-conductive adhesives, thermoplastic, epoxies, room-temperature-vulcanizing (RTV) silicone, or the like, or soldering, welding, bonding, crimping, press-fitting, or the like, or combinations thereof.

The core wire 360, including the straight portion 362, tapered end 365, and twisted portion 368, can include a heat shrink tube 346 disposed on an outer surface of the core wire 360. The heat shrink tube 346 can further secure the straight portion 362, tapered end 365, and twisted portions 368 of the core wire 360 together, and can further modify the stiffness profile along the length of the core wire 360. Each of the straight portion 362, tapered end 365, and twisted portion 368 of core wire 360 can provide differing stiffness profiles along the length of the stylet 340 while being formed of the same material and defining a substantially uniform cross-sectional area along the length of the stylet 340. For example, the straight portion 362 of the stylet 340 can provide an increased stiffness profile relative to the tapered end 365, or the twisted portion 368.

A magnet wire 370 can be twisted or braided around the core wire 360 and the heat shrink tube 346. The magnet wire 370 can be disposed about a portion of the straight portion 362, tapered end 365, or twisted portion 368 of the core wire 360, or combinations thereof. A polyimide sleeve, or outer jacket 344 can be disposed about the core wire 360, heat shrink tube 346, and magnet wire 370 to provide a smooth outer surface to the stylet 340. The stylet can further include a conductive tip 350 formed of either a conductive epoxy, bonded, or welded material similar to that of coupling 348. The conductive tip 350 can seal a distal end of the polyimide outer jacket 344 and provide a conductive pathway between a distal tip of the stylet 340 and the core wire 360. The core wire 360 can then provide a continuous electrical pathway along the entire length of stylet 340. It will be appreciated that, in an embodiment, a stylet 340 that does not include tracking capabilities can be formed without the magnet wire 370 and falls within the scope of the present invention.

Figure 4:
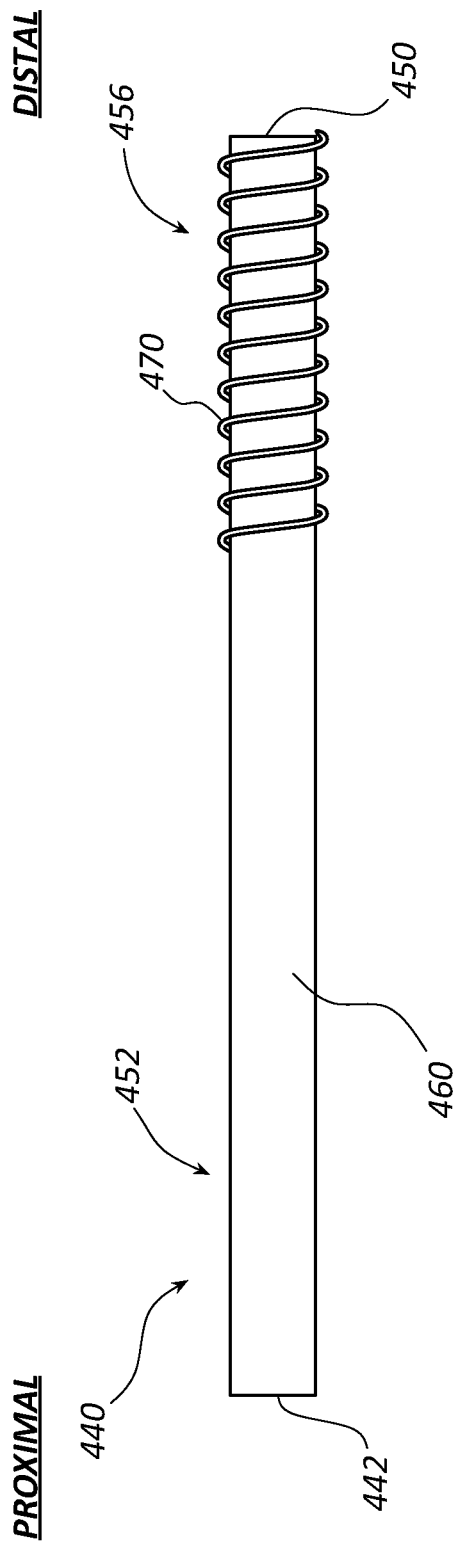
FIG. 4 is a side view of a stylet according to one embodiment.

FIG. 4 illustrates one embodiment of a stylet 440. The stylet 440 includes a core wire 460 and a magnet wire 470. The core wire 460 can include a proximal end 442 and a distal tip 450 and define a substantially straight outer profile, with a continuous cross-sectional diameter, therebetween. The core wire 460 can also include a proximal portion 452 and a distal portion 456. A magnet wire 470 can be twisted or braided about a distal portion 456 of the core wire 460. The core wire 460 provides a continuous conductive pathway between a distal tip 450 and a proximal end 442. The magnet wires 470 can vary the stiffness profile of the stylet 440. For example, the presence or absence of the magnet wire 470 between distal and proximal portions 456,452, respectively can affect the stiffness profile of the stylet 440. In an embodiment, differences in pitch, or number of turns, of the coil or braid of the magnet wire 470 can modify the stiffness profile of the stylet 440 along the length of stylet 440.

Figure 5:
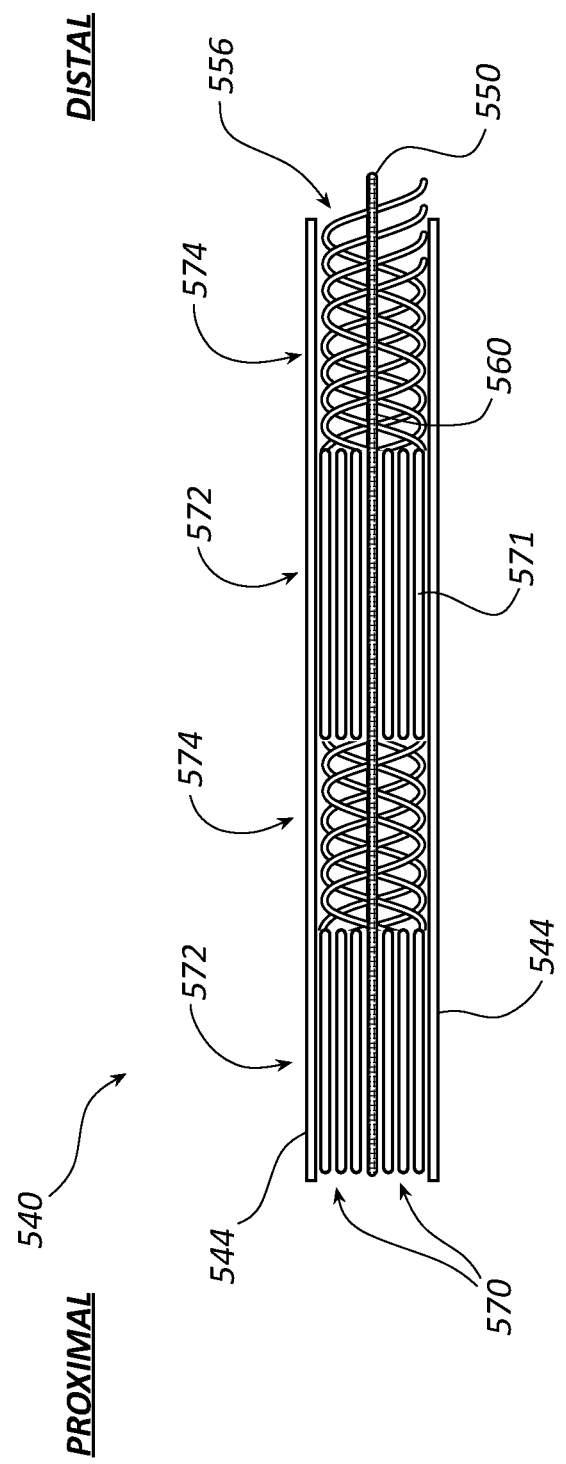
FIG. 5 is a side view of a stylet according to one embodiment.

FIG. 5 illustrates one embodiment of a stylet 540. The stylet 540 includes a core wire 560 and one or more wires 570. Wires 570 can be formed of the same, or similar material to core wire 560. It will be appreciated where stylet 540 includes electromagnetic tracking capabilities, one or more strands 571 of wires 570 can be a magnet wire. The one or more strands 571 of wires 570 can be "bundled" around the core wire 560 in layers, as described herein. The wires 570 can include a straight portion 572 and a twisted portion 574. It will be appreciated that stylet 540 can include more than one of each of the straight portion 572 and twisted portions 574. The straight portion 572 includes one or more strands 571 that extend parallel to the core wire 560 along a longitudinal axis. The twisted portion 574 can include one or more strands 571 that are twisted or braided about a longitudinal axis defined by the core wire 560. Each of the straight and twisted portions 572, 574 can provide differing stiffness characteristics along the length of the stylet 540. For example, the twisted portion 574 can provide more flexible characteristics than the straight portion 574.

The core wire 560 and wires 570 can terminate at the same distal position, e.g. distal portion 556. In an embodiment, a core wire 560 can extend beyond a distal end of the wires 570. In an embodiment, one or more strands 571 can terminate at different distal positions. For example, the outer layers of wires 570 can terminate at a first distal position and the inner layers of wires 570 can terminate at a second position, distal to the first distal position. In an embodiment, the core wire 560 can terminate at the second distal position or extend distally of the second distal position. The core wire 560 can terminate at a conductive tip 550 to provide a conductive pathway along the length of the stylet 540.

In an embodiment the straight portion 572 and the twisted portion 574 can have the same number of strands 571. In an embodiment the straight portion 572 and the twisted portion 574 can have a different number of strands 571. The total number of wires included in the stylet 540 can vary between 2 and 50, although it will be appreciated that greater numbers of wires can be included without deviating from the scope of the present invention. The diameter of the core wire 560 and individual strands 571 can have an outer diameter of between 0.001 in. (0.0254 mm) and 0.100 in. (2.54 mm), for example 0.010 in. (0.254 mm). In an embodiment, the core wire 560 can have the same diameter as one or more strands 571. The strands 571 can have a uniform diameter, or different diameters. For example, the wires could include a first set of wires at a first diameter, a second set of wires at a different second diameter, etc.

In an embodiment, stylet 540 can further include a sleeve 544 disposed on an outer surface of the stylet 540. The sleeve 544 can prevent the twisted portions from unraveling and maintain the straight wires in a packed formation about the core wire, as described herein. The sleeve 544 can also provide a smooth outer surface to the stylet 540. In an embodiment, sleeve 544 can extend over a portion of the stylet 540. In an embodiment, sleeve 544 can extend over a plurality of portions of the stylet 540, including the twisted portions 574 of the stylet 540. In an embodiment, sleeve 544 can include a heat shrink material, or polyimide material, although other materials are contemplated. In an embodiment, sleeve 544 can comprise a coiled wire that is electrically or magnetically permeable, or combinations thereof. For example, sleeve 544 can include a magnetic copper wire coiled around a portion of the stylet 540 to prevent the twisted portions from coming unraveled and maintain the straight wires in a packed formation about the core wire. In an embodiment the twisted portions 574 can include a knotted end (not shown). The knotted end can prevent the twisted portions 574 from coming unraveled. In an embodiment, the core wire 560 can include straight portions and twisted portions (not shown), similar to those of the wires 570, to further modify the stiffness characteristics of the stylet 540. The core wire straight and twisted portions can align with the straight and twisted portions 572, 574 of the magnet wire 570. In an embodiment, the core wire straight and twisted portions can be longitudinally offset from the straight and twisted portions 572, 574 of the magnet wire 570.

Figure 6:
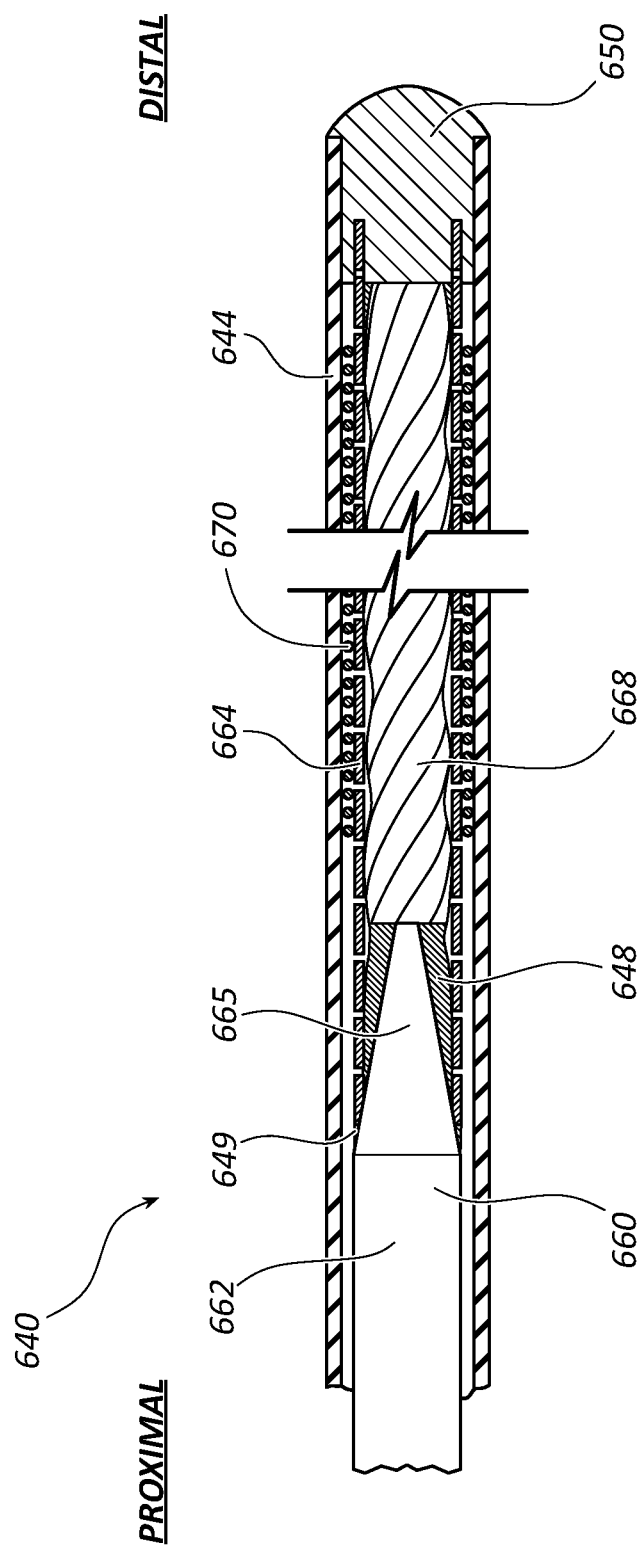
FIG. 6 is a side view of a stylet according to one embodiment.

FIG. 6 illustrates one embodiment of a stylet 640. The stylet 640 includes a core wire 660 and a magnet wire 670. The core wire 660 includes a straight portion 662, extending longitudinally and formed of a single monolithic wire, the straight portion terminating in a tapered end 665. The tapered end 665 can be coupled with a twisted portion 668. The twisted portion 668 can include two or more strands of core wire twisted or braided about each other. The twisted portion 668 can be coupled 648 with the tapered end 665 using adhesives, for example conductive or non-conductive adhesives, thermoplastic, epoxies, room-temperature-vulcanizing (RTV) silicone, or the like, or soldering, welding, bonding, crimping, press-fitting, or the like, or combinations thereof, as described herein.

The core wire 660 can further include a spring 664 extending longitudinally from the straight portion 662 to a conductive tip 650 disposed at a distal end of the stylet 640. The spring 664 consists of a wire, which defines a rectangular cross-section, and coils around the tapered end 665, twisted portion 668, and coupling 648. The spring 664 can be attached to the straight portion 662 of the core wire 660 using weld 649, although other attachment means such as adhesives, crimping, or press-fitting are also contemplated. The spring 664 can further secure the twisted portion 668 to the straight portion 662 of the core wire 660. The spring 664 can also further modify the stiffness profile of the core wire 660.

Each of the straight portion 662, spring 664 tapered end 665, and twisted portion 668 of core wire 660 can provide differing stiffness profiles along the length of the stylet 640 while being formed of the same material. For example, the straight portion 662 of the stylet 640 can provide an increased stiffness profile relative to the tapered end 665, spring 664, twisted portion 668 combinations, thereby allowing a clinician to easily handle and maneuver a proximal portion of the stylet 640 during catheter placement, while allowing a distal portion to negotiate tortuous vascular pathways.

A magnet wire 670 can be twisted or braided around the core wire 660. The magnet wire 670 can be disposed about a portion of the straight portion 662, spring 664, tapered end 665, or twisted portion 668 of the core wire 660, or combinations thereof. A polyimide outer jacket 644 can be disposed about the core wire 660, including the spring 644, and the magnet wire 670 combination to provide a smooth outer surface to the stylet 640. The stylet 640 can further include a conductive tip 650 formed of either a conductive epoxy, bonded, or welded material similar to that of coupling 648. The conductive tip 650 can seal a distal end of the polyimide outer jacket 644 and still provide a conductive pathway between a distal tip of the stylet 640 and the core wire 660. The core wire 660 can provide a continuous electrical pathway along the entire length of stylet 640. It will be appreciated that, in an embodiment, a stylet 640 that does not include tracking capabilities can be formed without the magnet wire 670 and falls within the scope of the present invention.

Figure 7:
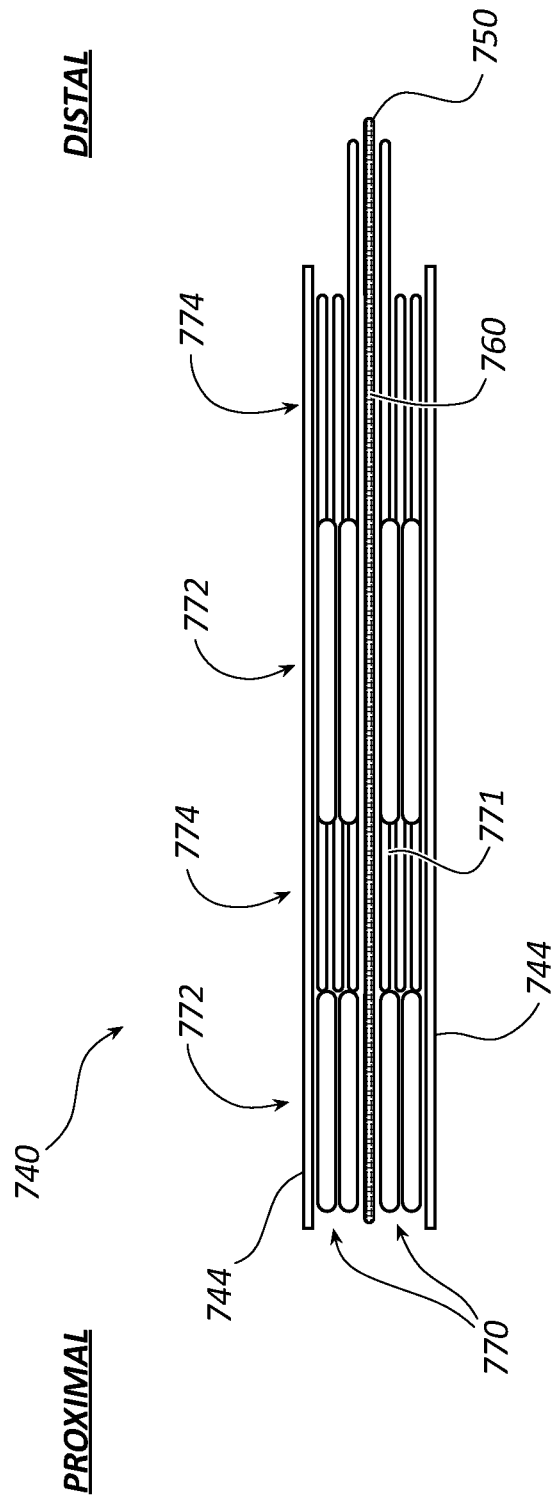
FIG. 7 is a side view of a stylet according to one embodiment.

FIG. 7 illustrates one embodiment of a stylet 740. The stylet 740 includes a core wire 760 and one or more strands 771 of wires 770. Wires 770 can be formed of the same, or similar material to core wire 760. It will be appreciated where stylet 740 includes electromagnetic tracking capabilities, one or more strands 771 of wires 770 can be a magnet wire. The wires 770 can be "bundled" around the core wire 760, as described herein. The wires 770 extend parallel to the core wire 760 along a longitudinal axis, and include a first portion 772 and a second portion 774. The first portion 772 includes wire strands 771 that each define a first diameter. The second portion 774 includes wire strands 771 that each define a second diameter. The first diameter can be larger than second diameter and the second portion 774 can include a greater number of wire strands 771 than the first portion 772. As such, a cross-sectional area of the stylet 740 remains substantially constant between a first portion 772 and a second portion 774. The different combinations of numbers of wires and differences in diameters for each of the wires between the first and second portions 772, 774 can provide different stiffness profiles along the length of the stylet 740. It will be appreciated that stylet 740 can include more than one of each of the first portion 772 and second portions 774.

The core wire 760 and wires 770 can terminate at the same distal position. In an embodiment, a core wire 760 can extend beyond a distal end of the wires 770. In an embodiment, one or more strands 771 can terminate at different distal positions. For example, outer layers of wires 770 can terminate proximally of adjacent inner layers. In an embodiment, the core wire 760 can terminate at the same position as adjacent layers of wires 770, or extend distally of the wires 770. The core wire 760 can terminate at a conductive tip 750. In an embodiment, stylet 740 can further include a sleeve 744 disposed on an outer surface of the stylet 740. The sleeve 744 can secure the wires 770 about the core wire 740 in a packed formation, and provide a smooth outer surface, as described herein.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein

What is claimed is:

1. A stylet, comprising:
   a core member formed of A228 carbon steel and extending between a proximal end and a distal tip, the core member defining a uniform cross-sectional area between the proximal end and the distal tip, the proximal end including a handle configured to remain outside of a body of a patient and the distal tip configured to be disposed inside of the body of the patient, a proximal portion of the core member formed of a single wire and defining a more rigid stiffness characteristic, and a distal portion of the core member formed of a plurality of wires and defining a more flexible stiffness characteristic, the core member configured to transmit an electrical signal from the distal tip to the handle; and
   a magnetic element disposed about a portion of the core member.

2. The stylet according to claim 1, wherein a material of the magnetic element includes copper.

3. The stylet according to claim 1, wherein the core member further includes a transition portion disposed between the proximal portion and the distal portion.

4. The stylet according to claim 3, wherein the transition portion includes a tapered monolithic portion and a coupling.

5. The stylet according to claim 4, wherein the coupling includes one of a conductive adhesive, a non-conductive adhesive, a thermoplastic, an epoxy, a room-temperature-vulcanizing (RTV) silicone, soldering, welding, bonding, crimping, or press-fitting.

6. The stylet according to claim 1, wherein the magnetic element includes one or more wires coiled or braided around the core member.

7. The stylet according to claim 6, wherein one or more of a wire diameter, a coil pitch, or a number of turns of the one or more wires of the magnetic element differs along a longitudinal axis of the stylet.

8. An elongate medical device, a portion configured to be inserted into a vasculature of a patient, the elongate medical device comprising:
   a core member formed of A228 carbon steel and extending between a proximal end and a distal tip and defining a uniform cross-sectional area between the proximal end and the distal tip, the proximal end supported by a handle configured to remain outside of the patient, the core member including:

a proximal portion formed as a single wire, extending parallel to a longitudinal axis of the elongate medical device, and defining a first stiffness characteristic; and a distal portion including a plurality of wires, defining a second stiffness characteristic, the core member configured to transmit an electrical signal between the proximal portion and the distal portion; and a magnetic element disposed on an outer surface of the core member.

9. The elongate medical device according to claim 8, wherein the proximal portion terminates in a tapered end and is coupled to the distal portion using one of a conductive adhesive, a non-conductive adhesive, a thermoplastic, an epoxy, a room-temperature-vulcanizing (RTV) silicone, soldering, welding, bonding, crimping, or press-fitting.

10. The elongate medical device according to claim 8, further including a sleeve disposed on the outer surface of the core member between the core member and the magnetic element, the magnetic element coiled or braided about the core member.

11. The elongate medical device according to claim 10, wherein the sleeve includes one of a polyimide jacket, or a heat shrink tube.

12. The elongate medical device according to claim 8, wherein the plurality of wires of the distal portion is one of coiled, braided, or twisted about each other.

13. The elongate medical device according to claim 8, further including a sleeve disposed on an outer surface of the magnetic element and including a conductive tip disposed at a distal end of the distal portion.

\* \* \* \* \*